(12) United States Patent
Fink et al.

(10) Patent No.: US 10,162,866 B2
(45) Date of Patent: Dec. 25, 2018

(54) IDENTIFYING POTENTIAL PATIENT CANDIDATES FOR CLINICAL TRIALS

(71) Applicant: International Business Machines Corporation, Armonk, NY (US)

(72) Inventors: Patrick W. Fink, Charlotte, NC (US); Kristin E. McNeil, Charlotte, NC (US); Philip E. Parker, York, SC (US); David B. Werts, Charlotte, NC (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/672,717

(22) Filed: Aug. 9, 2017

(65) Prior Publication Data

US 2017/0351816 A1 Dec. 7, 2017

Related U.S. Application Data

(63) Continuation of application No. 15/172,217, filed on Jun. 3, 2016.

(51) Int. Cl.
*G06F 17/30* (2006.01)
*G16H 10/20* (2018.01)
*G16H 10/60* (2018.01)
*G16H 40/63* (2018.01)
*G06F 17/28* (2006.01)

(52) U.S. Cl.
CPC ......... *G06F 17/3053* (2013.01); *G06F 17/28* (2013.01); *G06F 17/30864* (2013.01); *G16H 10/20* (2018.01); *G16H 10/60* (2018.01); *G16H 40/63* (2018.01)

(58) Field of Classification Search
CPC .......... G06F 17/3053; G06F 17/30864; G06F 17/28; G16H 10/20; G16H 10/60; G16H 40/63
USPC ....................................................... 705/2-3
See application file for complete search history.

(56) References Cited

U.S. PATENT DOCUMENTS

| | | | |
|---|---|---|---|
| 6,915,254 B1 * | 7/2005 | Heinze | G06F 17/27 382/225 |
| 8,285,703 B1 * | 10/2012 | Wagers | G06F 17/30011 707/709 |
| 8,630,868 B2 * | 1/2014 | Coutinho | G06F 19/3418 705/2 |

(Continued)

FOREIGN PATENT DOCUMENTS

| WO | 2016170368 A1 | 10/2016 |
| WO | 2016203457 A1 | 12/2016 |

OTHER PUBLICATIONS

Korkontzelos, Ioannis et al. "ASCOT: a text mining-based web-service for efficient search and assisted creation of clinical trials." BMC Med. Inf. & Decision Making (2012). (Year: 2012).*

(Continued)

*Primary Examiner* — Eliza A Lam
(74) *Attorney, Agent, or Firm* — Daniel C. Housley

(57) ABSTRACT

A computer system gleans data from patient records and clinical trial descriptions using NLP techniques. NLP annotation data is used to generate clinical trial feature vectors and patient feature vectors. Clinical trial feature vectors and patient feature vectors are compared to match appropriate patient candidates with clinical trial openings.

1 Claim, 6 Drawing Sheets

(56) References Cited

U.S. PATENT DOCUMENTS

| | | |
|---|---|---|
| 2004/0172447 A1 | 9/2004 | Miller |
| 2005/0203776 A1 | 9/2005 | Godwin et al. |
| 2005/0234740 A1 | 10/2005 | Krishnan et al. |
| 2006/0265248 A1* | 11/2006 | Barnhart ............... G06Q 30/04 |
| | | 705/2 |
| 2008/0195600 A1 | 8/2008 | Deakter |
| 2009/0089098 A1* | 4/2009 | Schoenberg ........... G06Q 50/22 |
| | | 705/3 |
| 2010/0161316 A1* | 6/2010 | Haug ................ G06F 17/2715 |
| | | 704/9 |
| 2012/0166209 A1 | 6/2012 | Lacal |
| 2012/0231959 A1 | 9/2012 | Elton et al. |
| 2012/0316898 A1 | 12/2012 | Levitt et al. |
| 2014/0006013 A1* | 1/2014 | Markatou ........... G06F 17/3061 |
| | | 704/9 |
| 2014/0188917 A1* | 7/2014 | Hopkins ........... G06F 17/30734 |
| | | 707/756 |
| 2014/0195170 A1 | 7/2014 | Avinash et al. |
| 2014/0310015 A1 | 10/2014 | Goldner |
| 2014/0316768 A1 | 10/2014 | Khandekar |
| 2014/0316793 A1 | 10/2014 | Pruit |
| 2015/0154372 A1 | 6/2015 | Soenksen et al. |
| 2015/0213234 A1 | 7/2015 | Dorsett et al. |
| 2016/0048655 A1* | 2/2016 | Maitra ................ G06F 19/3456 |
| | | 705/3 |
| 2016/0098389 A1* | 4/2016 | Bruno ................ G06F 17/2705 |
| | | 704/9 |
| 2016/0259826 A1* | 9/2016 | Acar ................ G06F 17/30867 |

OTHER PUBLICATIONS

Fink et al., "Identifying Potential Patient Candidates for Clinical Trials", U.S. Appl. No. 15/172,217, filed Jun. 3, 2016.
List of IBM Patents or Patent Applications Treated as Related, dated Aug. 8, 2017, pp. 1-2.

* cited by examiner

IDENTIFYING POTENTIAL PATIENT CANDIDATES FOR CLINICAL TRIALS

BACKGROUND

The present disclosure relates generally to the field of natural language processing (NLP), and more particularly to identifying potential patient candidates for clinical trials.

Selection of patient candidates for clinical trials requires reviewing patient records and clinical trial parameters and descriptions. For example, a principal investigator may review several clinical trial descriptions and thousands of patient records over the course of just as many hours in an effort to identify and contact a sufficient number of appropriate patient subjects for those clinical trials.

SUMMARY

Disclosed herein are embodiments of a method, system, and computer program product for matching clinical trial openings with candidates from a patient population. A first clinical trial description is identified. Natural language processing techniques, including one or more annotators, are applied to the first clinical trial description to generate annotations of the first clinical trial description. A first trial feature vector is generated based on the annotations of the first clinical trial description, the first trial feature vector comprising a first array of values, each representing a clinical feature. A comparison value is generated based on the first trial feature vector and a first patient feature vector, the first patient feature vector comprising a second array of values, wherein the first patient feature vector is generated using annotations of a patient record, the annotations of the patient record generated by applying natural language processing techniques, including the one or more annotators, to the patient record. Information about a patient associated with the patient record is displayed to a user based on the comparison value.

The above summary is not intended to describe each illustrated embodiment or every implementation of the present disclosure.

BRIEF DESCRIPTION OF THE DRAWINGS

The drawings included in the present disclosure are incorporated into, and form part of, the specification. They illustrate embodiments of the present disclosure and, along with the description, serve to explain the principles of the disclosure. The drawings are only illustrative of typical embodiments and do not limit the disclosure.

DETAILED DESCRIPTION

Aspects of the present disclosure relate to natural language processing (NLP), and more particularly to identifying potential patient candidates for clinical trials. While the present disclosure is not necessarily limited to such applications, various aspects of the disclosure may be appreciated through a discussion of various examples using this context.

Identifying patient candidates that are appropriate for any given clinical trial can be time-intensive when done manually. It is difficult for patients to know about clinical trials and their criteria. While physician investigators can have access to large patient pools and clinical trial descriptions, it is difficult for this information to be distributed across investigators in the medical community.

Investigators recruit potential patient candidates via patient surveys or other investigator-patient or provider-patient interactions, which consumes time and resources for all parties involved. However, a large amount of patient information needed to assess a potential candidate may be in the semi-structured or unstructured text of the candidate's patient records. NLP can be employed to glean data from patient records, possibly eliminating or reducing the need for direct investigator-patient or provider-patient interactions, patient surveys, phone calls, etc. and conserving labor hours and costs.

Various embodiments are directed toward a computer system that may identify appropriate patient candidates for clinical trials based on information from the structured, semi-structured, and unstructured text of clinical trial descriptions and patient records. As discussed herein, NLP may be utilized to convert source text into annotated text. In embodiments, the annotations in the annotated text may be used to generate a feature vector. A feature vector may be, for example, an array of values where each value indicates the presence or absence of a particular annotation. In embodiments, patient feature vectors may be compared against clinical trial feature vectors to generate a comparison value. This comparison may be performed, for example, using distance metrics (e.g. Euclidian, Mahalanobis, Manhattan, etc.) to calculate the logical distance between the two vectors. The comparison value may indicate the degree to which the patient is an appropriate candidate for the clinical trial. Information may be displayed to a user based on the comparison value.

Figure 1:
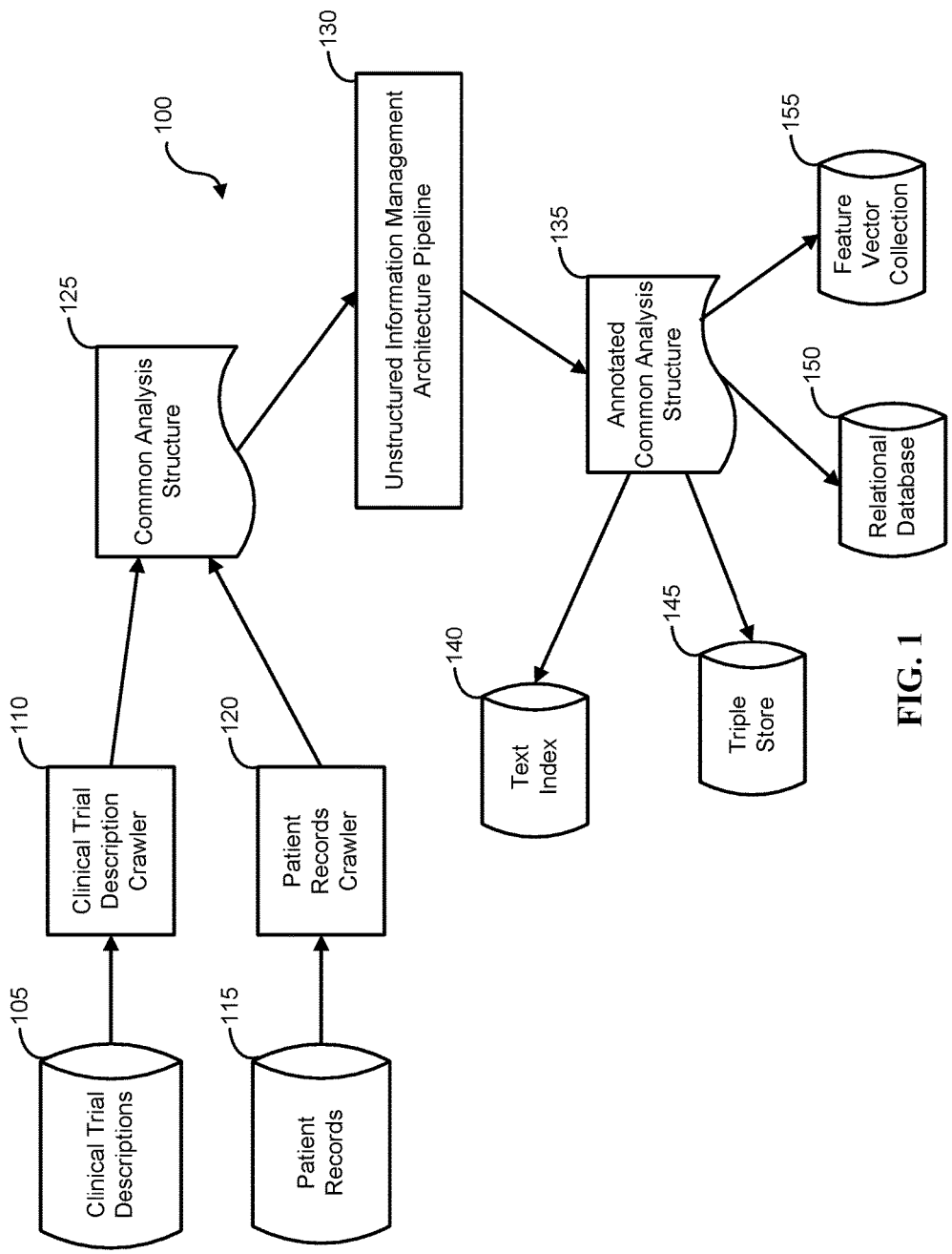
FIG. 1 illustrates a high level flow diagram of a content analytics process for clinical trial descriptions and patient records, including Unstructured Information Management Architecture (UIMA) standards, according to embodiments.

The present disclosure will now be described in detail with reference to the Figures. FIG. 1 is a high-level flow diagram illustrating a content analytics process for clinical trial descriptions and patient records, including Unstructured Information Management Architecture (UIMA) standards, according to embodiments. From their respective storages 105 and 115, clinical trial descriptions and patient records are retrieved by their respective crawlers 110 and 120. For example, a description of a clinical trial testing the effectivity of Drug X may reside in a research laboratory's database of clinical trial descriptions. A patient record for patient John Doe may reside in a hospital database of patient records. Crawlers can be configured to identify and retrieve these documents. For example, a crawler may be configured to identify and retrieve a patient record based on textual similarities with a clinical trial description, file name extension, keyword presence, etc. Crawlers may be configured to "crawl" through a database at a given interval, and/or to retrieve documents that have been updated or modified subsequent to a previous retrieval. A document fitting the crawler's parameters may be retrieved, analyzed, and converted, resulting in a standardized format. For example, a Common Analysis Structure (CAS) at 125. A CAS 125 may be a document, for example, a patient record or clinical trial description that has been converted into a standard format in preparation for an NLP operation, for example, processing via UIMA, General Architecture for Text Engineering, Natural Language Toolkit, etc.

The CAS 125 may be processed through a UIMA pipeline at 130. The UIMA pipeline 130 may include several modules, each performing a particular operation. For example, a module may identify the language used in the CAS 125, another may analyze syntactic structure, yet another may apply a custom annotator configured to look for the presence or absence of particular features, etc.

The result of the UIMA pipeline 130 produces an annotated CAS at 135. For example, an annotated CAS 135 may contain annotation data allowing a computer system to identify the content and meaning of the source text in the original document. For clinical trial descriptions and patient records, the annotations may represent clinical features, disease states, the relationship between disease markers and the stage of disease progression, the relationship between a particular patient and a particular medical professional, etc.

Annotated CASs 135 may then be used to populate text indices 140, triple stores 145, relational databases 150, and/or feature vector collections 155.

Figure 2:
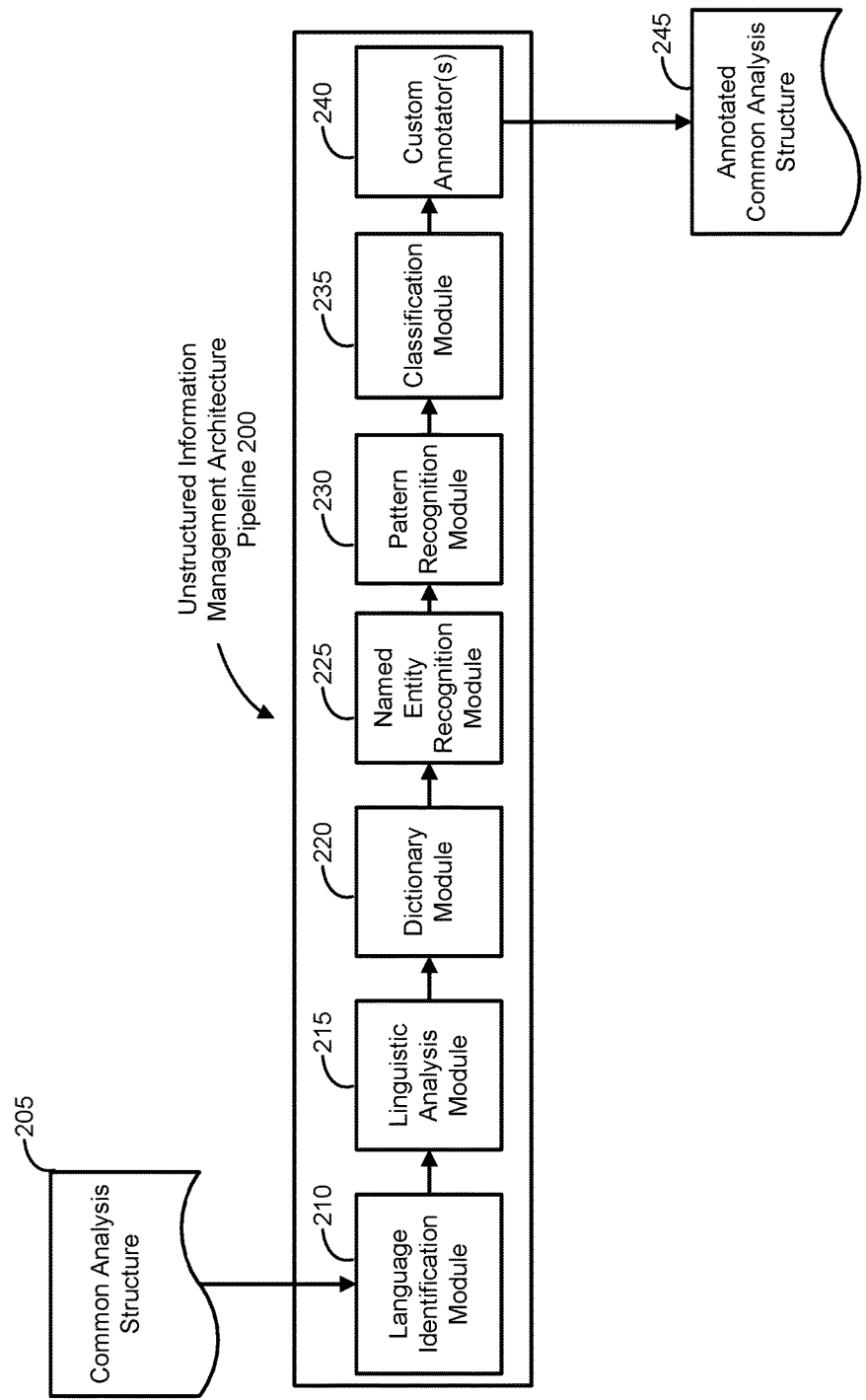
FIG. 2 illustrates a flowchart depicting operations of a UIMA pipeline, according to embodiments.

FIG. 2 illustrates a flowchart depicting operations of a UIMA pipeline 200, according to embodiments. The modules 210-240 of the present disclosure may be one or more instructions, routines, fixed function circuits, etc., that may be executed by a process and read from a memory (e.g., the computer of FIG. 6). A CAS 205 is analyzed by a language identification module at 210. For example, a patient record written in English may be identified as such, allowing the following modules to accurately apply English-specific linguistic rules, definitions, patterns, etc. A patient record written in Czech may be identified as such, allowing for the following modules to apply Czech-specific linguistic rules, definitions, patterns, etc.

The CAS 205 is processed by a linguistic analysis module 215, which may annotate the parts of speech. For example, nouns, verbs, adjectives, etc. are labeled as such.

Dictionary module(s), are applied at 220, matching words, phrases, and their synonyms in dictionaries with the words in the CAS 205. For example, a clinical dictionary may include terms for diseases, drugs, therapies, medical devices, etc. The term "acetaminophen" may be labeled as a noun, a "drug name," a "drug," etc.

The CAS 205 is processed by a named entity recognition module at 225. For example, the named entity recognition module may identify proper nouns, such as person names, location names, company names, etc. Rules may be written and used to identify particular entity types, such as: "The noun following the words 'lives in' is a location." In this example, the CAS 205 may be annotated to indicate the word identified by the rule is a noun of the "location" type.

The CAS 205 is processed by a pattern recognition module at 230. For example, patterns may be used to identify concepts (e.g. a patient is healthy) rather than simple words (e.g. patient, health) or word strings. Consider the following sentence: "The patient is healthy." Simple word annotations would recognize the words singly, and allow the source text (e.g., patient record) to be displayed when the terms "patient" or "healthy" are searched, but such a search may often return many more results than needed, such as when a user wished to search for a document containing the concept of "a healthy patient." Likewise, searching for a word string "healthy patient" may not return those documents describing a patient as "not unhealthy," "in the peak of fitness," etc. As such, the pattern recognition module may use rules to identify concepts over simple words or word strings. For example, "[patient name]+[be]+ [negative term]=unhealthy," or "[patient name]+[be]+[not]+ [positive term]=unhealthy."

The CAS 205 is processed by a classification module at 235. For example, a classification module sorts documents based on their content. Classification modules may be trained by supplying the module with examples of documents in the various categories/classifications desired. For example, the module may learn to distinguish auto body shop invoices from tax returns from restaurant menus by supplying it with, and allowing it to analyze, a number of each type of document. The module may then attempt to correctly classify new documents as one of these types based on the content of previously-analyzed documents.

The CAS 205 is then processed by one or more custom annotators at 240. For example, a user may configure a custom annotator to identify statistical data or to label keywords, patterns, etc. in any way they choose. For example, a rule-based annotator may label a pattern coding for the presence of an influenza infection, the absence of a *Streptococcus aureus* infection, the presence of a simian crease, etc. A statistical-based annotator may identify an ambiguous phrase and use, for example, a corpora of previously-encountered text or probabilistic model to annotate the ambiguous phrase with a possible definition. The annotations may be converted into numerical values to populate feature vectors, as described herein.

After being processed by the custom annotators, the CAS 205 emerges from the UIMA pipeline as an annotated CAS at 245. For example, the CAS 205 may be annotated, such that a computer system may now identify it by language; identify the various parts of speech; identify the definitions of the words/phrases; identify which nouns are proper nouns; identify which nouns pronouns refer to, based on pattern matching; classify the document based on previous document types processed; and identify/characterize source texts as identified and defined by the custom annotators.

Figure 3:
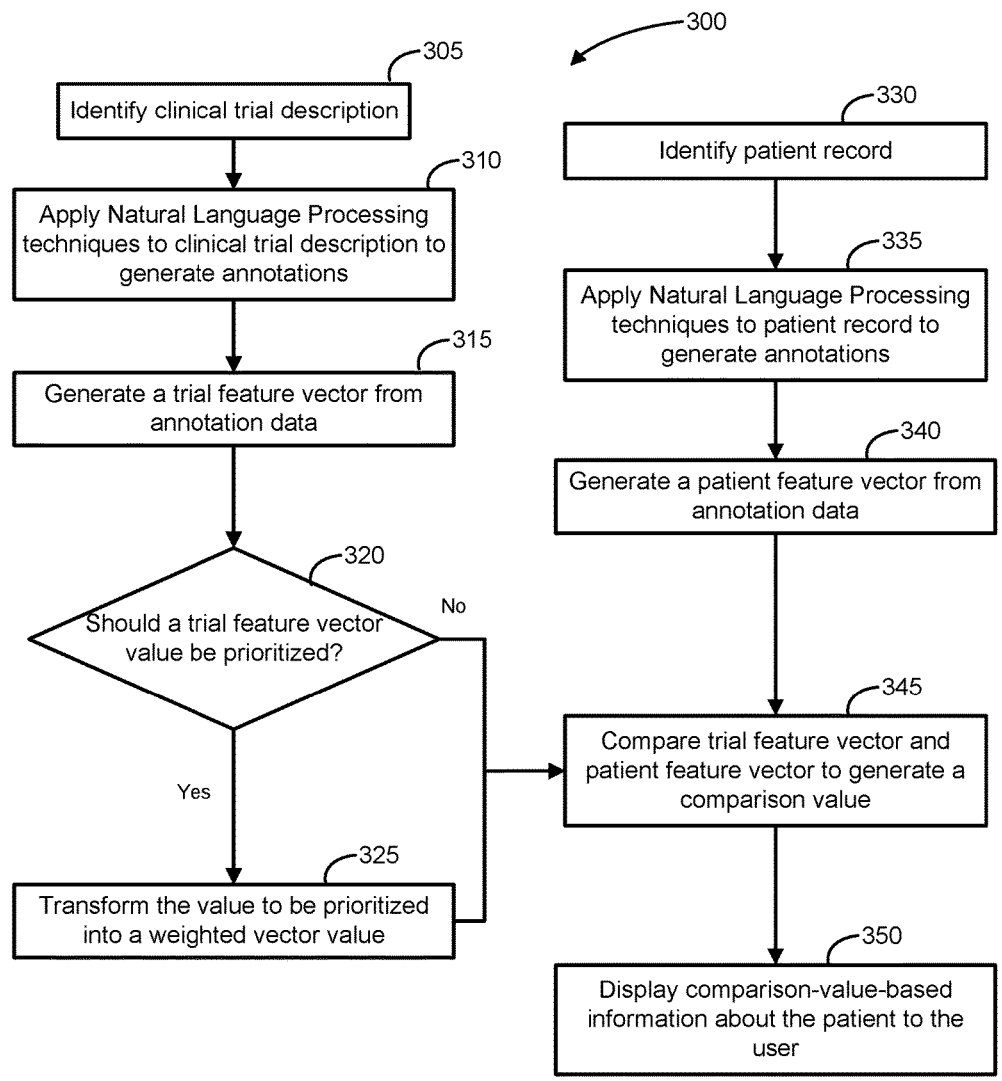
FIG. 3 depicts a flow diagram of a method for generating and displaying a comparison value using NLP and feature vectors based on annotations, according to embodiments.

FIG. 3 depicts a flow diagram of a computer-implemented method 300 for generating and displaying a comparison value using NLP and feature vectors based on annotations, according to embodiments. At 305, a clinical trial description is identified. For example, Document XYZ may describe a clinical trial measuring the effectivity of doses 10 mg, 20 mg, and 45 mg of Drug X on a patient population presenting as 20-40, male, with Condition Y. However, patients already taking Drug Z are not acceptable candidates.

At 310, NLP techniques are applied to the clinical trial description to generate annotations. For example, Document XYZ may be processed through a UIMA pipeline as described in FIG. 2 to generate an annotated CAS, wherein the custom annotators have identified the characteristics of ideal patient candidates, for example, in Document XYZ, age range 20-40, male, having Condition Y, and not taking Drug Z.

At 315, a trial feature vector is generated from the annotation data. For example, the aforementioned characteristics of idea patient candidates in Document XYZ may be used to generate an array of values, wherein the values represent the presence/absence of the characteristics. For example, [age, gender, Condition Y, Drug Z], wherein the trial feature vector (e.g., the ideal candidate; e.g., a 20-40 year-old, male, has Condition Y, not taking Drug Z) may be represented by [1,1,1,1].

If, at 320, it is determined that a trial feature vector should be prioritized, then the corresponding value is transformed into a weighted vector value at 325. For example, in Document XYZ, if it's determined that not taking Drug Z should be a prioritized feature, then the value representing the patient not taking Drug Z may be weighted. For example, the trial feature vector (e.g., the ideal candidate; e.g., a 20-40 year-old, male, has Condition Y, not taking Drug Z) may instead be represented by [1,1,1,2].

At 330, a patient record is identified. A patient record may be a document with clinical significance for a given patient. For example, patient John Doe's annual wellness checkup report, vaccination record, laboratory results, etc.

At 335, NLP techniques are applied to the patient record to generate annotations. For example, a CAS generated from John Doe's annual wellness checkup report may be processed through a UIMA pipeline as described in FIG. 2 to generate an annotated CAS, where custom annotators generated annotations of John Doe's clinical features.

At 340, a patient feature vector is generated from the annotations. For example, a patient's annotations may be used to generate an array of values representing the presence or absence of certain clinical features (e.g., clinical terms, disease states, diagnoses, demographics, etc.). For example, if John Doe is an 18 year-old male with Condition Y, and it is not known whether he takes Drug Z, then John Doe's patient feature vector may be represented as [−1,1,1,0].

After trial feature vector prioritization, or if it is determined at 320 that prioritization is unnecessary, the trial feature vector is compared with a patient feature vector at 345 to generate a comparison value. For example, the trial feature vector from Document XYZ, [1,1,1,2], may be compared to the patient feature vector of John Doe, [−1,1,1,0], to yield a comparison value. For example, the comparison value may be calculated using distance metrics (e.g. Euclidean, Mahalanobis, Manhattan, etc.) to represent the logical distance between John Doe's patient feature vector and the trial feature vector from Document XYZ.

At 350, information is displayed to the user, based on the comparison value. For example, patient names of multiple patients whose feature vectors have been compared to a particular trial feature vector may be displayed, sorted by minimal logical distance, using an interactive user interface. For example, John Doe's name may be listed with other patient names, where John Doe's name may be listed below Jeremy Doe, a patient whose comparison value represents a smaller logical distance to the trial feature vector, and above Jane Doe, a patient whose comparison value represents a greater logical distance to the trial feature vector. The information displayed may be filtered and sorted, in response to a user interaction (e.g., selecting a filter option, typing a keyword into a field, etc.), using a threshold comparison value limitation to display only the information of patients whose comparison value meets the threshold comparison value. The information may also be filtered and sorted, in response to a user interaction, for display based on patient name, contact information, geographical region, disease type, clinical feature, etc.

Figure 4:
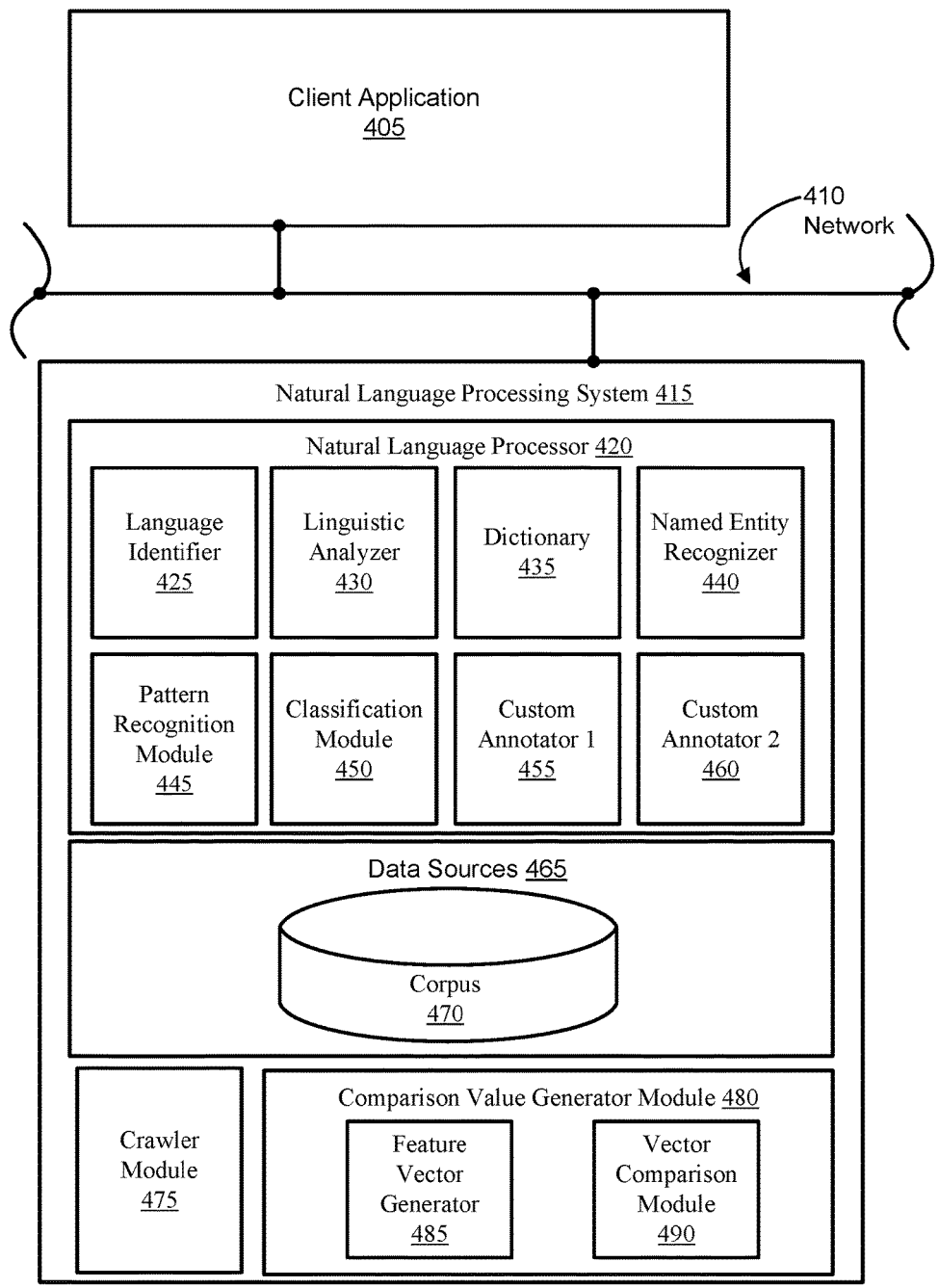
FIG. 4 depicts a block illustration of an example system architecture, including a natural language processing system, configured to analyze clinical trial descriptions and patient records to generate feature vectors and comparison values, according to embodiments.

FIG. 4 depicts a block illustration of an example system architecture 400, including a natural language processing system, configured to analyze clinical trial descriptions and patient records to generate feature vectors and comparison values, according to embodiments. In embodiments, a user may use a remote device (such as remote device 510 of FIG. 5) to submit clinical trial descriptions, custom annotators, etc. to be used by the NLP system 415 which may be housed on a host device (such as host device 545 of FIG. 5). A host device may be, for example, a server, a computer, a laptop, or any other device capable of executing a content analytics process, as described herein. A remote device (e.g., remote device 510 of FIG. 5) may include a client application 405, which may itself involve one or more entities operable to receive, generate, or modify clinical trial descriptions, custom annotators, etc. that may then be dispatched to NLP system 415 via a network 410. A remote device may be, for example, a computer, a laptop, a smartphone, a tablet, etc.

In embodiments, the natural language processing system 415 may respond to submissions from client application 405. Specifically, the NLP system 415 may analyze clinical trial descriptions to identify characteristics about the received content (e.g., clinical features, ideal candidate attributes, etc.). In some embodiments, the NLP system 415 may include a natural language processor 420, data sources 465, a crawler module 475, and a comparison generator module 480. The natural language processor 420 may be a computer module that analyzes the received content. The natural language processor 420 may perform various methods and techniques for analyzing the received content (e.g., syntactic analysis, semantic analysis, etc.). The natural language processor 420 may be configured to recognize and analyze any number of languages. In some embodiments, the natural language processor 420 may parse passages of the received content. Further, the natural language processor 420 may include various modules to perform analyses of electronic documents (e.g., clinical trial descriptions, patient records, etc.). These modules may include, but are not limited to, a language identifier 425, a linguistic analyzer 430, a dictionary 435, a named entity recognizer 440, a pattern recognition module 445, a classification module 450, and any number of custom annotators 455 and 460.

In some embodiments, the language identifier may be a computer module that determines a document's language. The language identifier 425 may utilize one or more methods for determining the language of a particular document. The language identifier 425 may compare the compressibility of the test to the compressibility of texts in a set of known languages via a mutual information based distance measure technique. The language identifier 425 may utilize n-gram models from a set of texts of known languages for comparison against an n-gram model created from the text of the document of unknown language. The language identifier 425 may analyze the prevalence of "function words" (e.g., "the" in English) to identify a document's language.

Consistent with various embodiments, the linguistic analyzer 430 may be a computer module that marks up words in passages to correspond to particular parts of speech, syntactic position and function, etc. The linguistic analyzer 430 may read a passage or other text in natural language and assign a part of speech or syntactic annotation to each word or string of words. The linguistic analyzer 430 may determine the part of speech or syntactic function to which a word (or other text element) corresponds based on the definition of the word and the context of the word. The context of a word may be based on its relationship with adjacent and related words in a phrase, sentence, or paragraph. In some embodiments, the context of a word may be dependent on one or more previously analyzed documents (e.g., the content of one social media post may shed light on the meaning of text elements in related social media post, or content of a first comment by a user on an Internet forum may shed light on meaning of text elements of a second comment by that user on the same or different Internet forum). Examples of parts of speech that may be assigned to words include, but are not limited to, nouns, verbs, adjectives, adverbs, and the like. Examples of other part of speech categories that linguistic analyzer 430 may assign include, but are not limited to, comparative or superlative adverbs, wh-adverbs, conjunctions, determiners, negative particles, possessive markers, prepositions, wh-pronouns, and the like. In some embodiments, the linguistic analyzer 430 may tag or otherwise annotate words with syntactic positions and functions, such as subject, predicate, verb, prepositional phrase, direct object, indirect object, genitive case, etc.

In embodiments, the dictionary 435 may be a computer module that may be configured to identify the definitions of words and phrases. In some embodiments, the dictionary 435 may identify functional equivalents (e.g., synonyms) between words and phrases.

In embodiments, the named entity recognizer 440 may be a computer module that is configured to identify proper nouns, and pronouns referring to proper nouns, in a document. The named entity recognizer 440 may determine the nature of a noun via dictionary definition, context, or word attribute and position (e.g. a capitalized noun, not being the first word of a sentence, in the subject position).

In embodiments, the pattern recognition module 445 may be a computer module that is configured to identify patterns in the text. For example, the pattern recognition module 445 may be configured to identify any string of numbers in the format: (XXX)XXX-XXXX as a telephone number, or a five-digit number following a state abbreviation as a zip code. The pattern recognition module 445 may be configured to identify concepts conveyed by words and phrases as described herein.

In embodiments, the classification module 450 may be a computer module that is configured to categorize a document based on the document's content. As described herein, the classification module may be trained to identify a document type based on previously-analyzed documents.

In embodiments, the custom annotators 455 and 460 may be computer modules that are configured to serve a specific, user-defined purpose. For example, custom annotators 455 and 460 may tag a particular word or phrase and count the number of times the word or phrase is used and report this to a user. Custom annotators may identify statistical data from structured or semi-structured text. Custom annotators 455 and 460 may use the presence or absence of terms or features and/or statistical data to generate a set of standardized annotations for use in generating feature vectors, which may then be compared to the feature vectors of other documents to determine logical distance between the two feature vectors. Custom annotators 455 and 460 may identify ambiguous pronouns in a document and display them to a user. In embodiments, any number of custom annotators may be used.

In some embodiments, the natural language processor 420 may be a computer module that parses received content and generates corresponding annotated data structures for one or more portions of the received content. For example, in response to receiving a set of email exchanges at the natural language processing system 420, the natural language processor 420 may output parsed and annotated text elements from the email messages as data structures. In some embodiments, a parsed and annotated text element may be represented in the form of a parse tree or other graph structure. To generate the parsed and annotated text element, the natural language processor 420 may trigger computer modules 425-460.

In some embodiments, the output of natural language processor 420 (e.g., annotated documents) may be stored within data sources 465, such as corpus 470. As used herein, a corpus may refer to one or more data sources, such as the data sources 465 of FIG. 4. In some embodiments, the data sources 465 may include data warehouses, corpora, data models, statistical reports, and document repositories. In some embodiments, the corpus 470 may be a text index, relational database, triple store, feature vector collection, or any other means for storing data associated with annotations.

In embodiments, the crawler module 475 may search data sources 465 including the corpus 470 of ingested data. The crawler module 475 may search the data sources 465 for data relevant to the comparison value generation, including standardized annotations for use in generating feature vectors. In embodiments, the comparison value generator module 480 may be a computer module that generates one or more comparison values based on annotations from ingested data including feature vectors generated from those annotations.

In some embodiments, the comparison value generator module 480 may include a feature vector generator 485 and a vector comparison module 490. The feature vector generator 485 may identify standardized annotations associated with ingested content (e.g., clinical trial descriptions, patient records, etc.). In embodiments, this identification may be conducted over only the data identified as relevant based on the results of the search by the crawler module 475. The feature vector generator 485 may generate an array of values to represent annotations associated with particular clinical features, as described herein. Annotations associated with features that should be prioritized may be weighted more heavily than others, as described herein.

In some embodiments, after the feature vector generator 485 generates a feature vector as described herein, the vector comparison module 490 may compare two feature vectors. For example, the vector comparison module may utilize one or more distance metric calculation techniques (Euclidian, Mahalanobis, Manhattan, etc.) to generate a comparison value representing the logical distance between the trial feature vector associated with Document XYZ and the patient feature vector associated with John Doe. The comparison value may be used to display patient information to a user, sorted in order of minimal logical distance.

Figure 5:
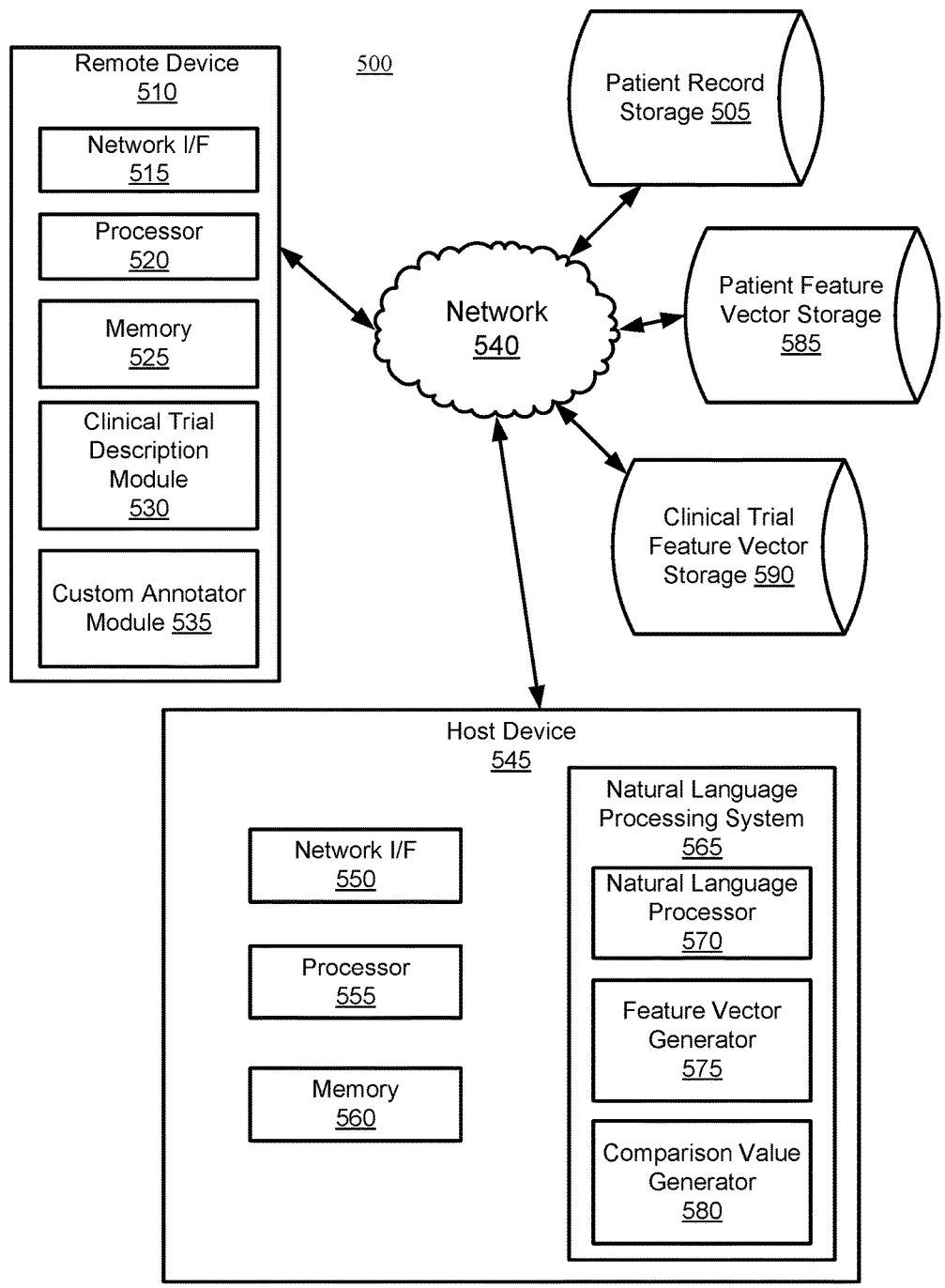
FIG. 5 depicts a block diagram of an example computing environment in which embodiments of the present disclosure may be implemented.

FIG. 5 depicts a block diagram of an example computing environment 500 in which embodiments of the present disclosure may be implemented. In embodiments, the computing environment 500 may include a remote device 510 and a host device 545. In some embodiments, functions of remote device 510 and host device 545 may be implemented using a single device.

According to embodiments, the host device 545 and the remote device 510 may be computer systems. The remote device 510 and the host device 545 may include one or more processors 520 and 555 and one or more memories 525 and 560, respectively. The remote device 510 and the host device 545 may be configured to communicate with each other through an internal or external network interface 515 and 550. The network interfaces 515 and 550 may be, e.g., modems, wireless network adapters, Ethernet adapters, etc. The remote device 510 and/or the host device 545 may be equipped with a display or monitor. Additionally, the remote device 510 and/or the host device 545 may include optional input devices (e.g., a keyboard, mouse, scanner, or other input device), and/or any commercially available or custom software (e.g., browser software, communications software, server software, NLP software, search engine, and/or web crawling software, filter modules for filtering content based upon predefined parameters, etc.). In some embodiments, the remote device 510 and/or the host device 545 may be servers, desktops, laptops, or hand-held devices.

The remote device 510 and the host device 545 may be distant from each other and may communicate over a network 540. In embodiments, the host device 545 may be a central hub from which a remote device 510 and other remote devices (not pictured) can establish a communication connection, such as in a client-server networking model. In some embodiments, the host device 545 and remote device 510 may be configured in any other suitable network relationship (e.g., in a peer-to-peer configuration or using another network topology).

In embodiments, the network 540 can be implemented using any number of any suitable communications media. For example, the network 540 may be a wide area network (WAN), a local area network (LAN), the Internet, or an intranet. In certain embodiments, the remote device 510 and the host device 545 may be local to each other, and communicate via any appropriate local communication medium. For example, the remote device 510 and the host device 545 may communicate using a local area network (LAN), one or more hardwire connections, a wireless link or router, or an intranet. In some embodiments, the remote device 510, the host device 545, and any other devices may be communicatively coupled using a combination of one or more networks and/or one or more local connections. For example, the remote device 510 may be hardwired to the host device 545 (e.g., connected with an Ethernet cable) while a second device (not pictured) may communicate with the host device using the network 540 (e.g., over the Internet).

In some embodiments, the network 540 can be implemented within a cloud computing environment, or using one or more cloud computing services. Consistent with various embodiments, a cloud computing environment may include a network-based, distributed data processing system that provides one or more cloud computing services. Further, a cloud computing environment may include many computers (e.g., hundreds or thousands of computers or more) disposed within one or more data centers and configured to share resources over the network 540.

In some embodiments, the remote device 510 may enable users to submit (or may submit automatically with or without a user selection) clinical trial descriptions, custom annotators, etc. to the host device 545. In some embodiments, the user may enter and/or submit clinical trial descriptions via a clinical trial description module 530. In some embodiments, the user may enter and/or submit custom annotators via a custom annotator module 535. In some embodiments, the host device 545 may include an NLP system 565. The NLP system 565 may include a natural language processor 570, a feature vector generator 575, and a comparison value generator 580. The natural language processor 570 may include numerous subcomponents, such as a language identifier, a linguistic analyzer, a dictionary, a named entity recognizer, pattern recognition module, classification module, and custom annotator(s) (such as the natural language processor 420 in FIG. 4). The natural language processor 570 may be configured to perform NLP techniques by ingesting a clinical trial description and utilizing custom annotator(s) submitted by remote device 510. In some embodiments, the natural language processor 570 may retrieve patient records for NLP application from patient record storage 505.

In some embodiments, the feature vector generator 575 be implemented using a custom annotator to generate feature vectors from annotations directly. In some embodiments, the feature vector generator may be implemented using a feature vector generator as part of a comparison value generator module, as described herein, and seen in FIG. 4. In some embodiments, the feature vector generator may retrieve and/or store clinical trial feature vectors and/or patient feature vectors using clinical trial feature vector storage 590 and patient feature vector storage 585, respectively. Patient record storage 505, patient feature vector storage 585, and clinical trial feature vector storage 590 may be implemented using remote storage devices accessed over a network 540, using local storage on remote device 510 or host device 545, or using any other operable configuration (e.g., using storage media).

The comparison value generator 580 may be configured to analyze a set of feature vectors generated by the feature vector generator 575, to generate comparison values which may be sorted. Information associated with one or more of the comparison values may be displayed to the user of the remote device 510. The comparison value generator 580 may include one or more modules or units, and may utilize the feature vector generator 575, to perform its functions (e.g., to determine a logical distance between a clinical trial description and a patient record), as discussed in more detail in reference to FIG. 4.

While FIG. 5 illustrates a computing environment 500 with a single host device 545, a single remote device 510, a single patient record storage 505, a single patient feature vector storage 585, and a single clinical trial feature vector storage 590, suitable computing environments for implementing embodiments of this disclosure may include any number of remote devices, host devices, patient record storage devices, patient feature vector storage devices, and clinical trial feature vector storage devices. The various models, modules, systems, and components illustrated in FIG. 5 may exist, if at all, across a plurality of devices. For example, some embodiments may include two remote devices or two host devices. The two host devices may be communicatively coupled using any suitable communications connection (e.g., using a WAN, a LAN, a wired connection, an intranet, or the Internet). The first host device may include a natural language processing system configured to receive and analyze content from patient record storage 505, and the second host device may include a natural language processing system configured to receive and analyze clinical trial descriptions and apply custom annotators, the descriptions received from the first remote device, and the custom annotators received from the second remote device.

It is noted that FIG. 5 is intended to depict the representative major components of an exemplary computing environment 500. In some embodiments, however, individual components may have greater or lesser complexity than as represented in FIG. 5, components other than or in addition to those shown in FIG. 5 may be present, and the number, type, and configuration of such components may vary.

Figure 6:
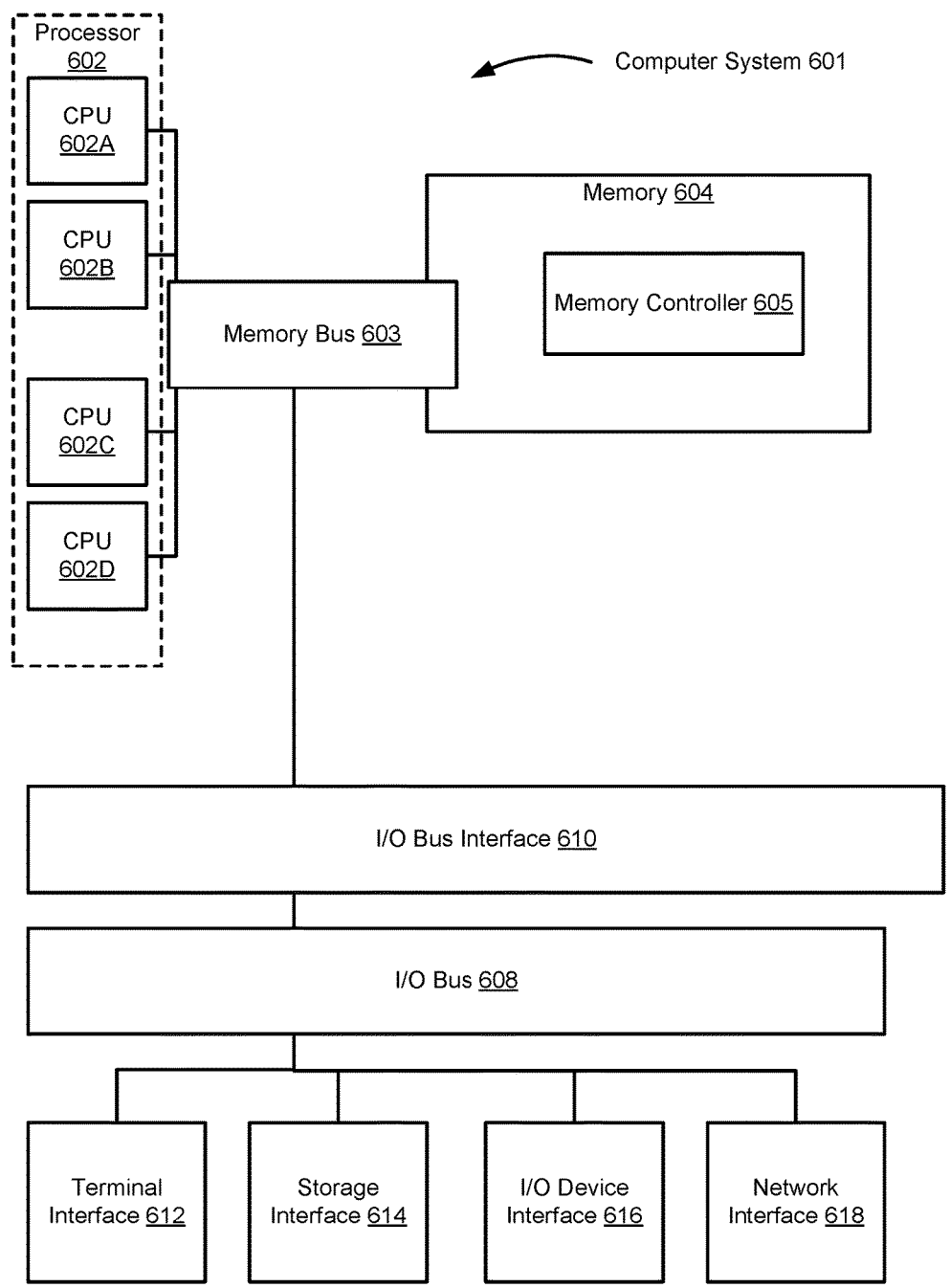
FIG. 6 illustrates a high-level block diagram of an example computer system that may be used in implementing embodiments of the present disclosure.

Referring now to FIG. 6, shown is a high-level block diagram of an example computer system (i.e., computer) 601 that may be configured to perform various aspects of the present disclosure, including, for example, method 300, described in FIG. 3. The example computer system 601 may be used in implementing one or more of the methods or modules, and any related functions or operations, described herein (e.g., using one or more processor circuits or computer processors of the computer), in accordance with embodiments of the present disclosure. In some embodiments, the major components of the computer system 601 may comprise one or more CPUs 602, a memory subsystem 604, a terminal interface 612, a storage interface 614, an I/O (Input/Output) device interface 616, and a network interface 618, all of which may be communicatively coupled, directly or indirectly, for inter-component communication via a memory bus 603, an I/O bus 608, and an I/O bus interface unit 610.

The computer system 601 may contain one or more general-purpose programmable central processing units (CPUs) 602A, 602B, 602C, and 602D, herein generically referred to as the CPU 602. In some embodiments, the computer system 601 may contain multiple processors typical of a relatively large system; however, in other embodiments the computer system 601 may alternatively be a single CPU system. Each CPU 602 may execute instructions stored in the memory subsystem 604 and may comprise one or more levels of on-board cache.

In some embodiments, the memory subsystem 604 may comprise a random-access semiconductor memory, storage device, or storage medium (either volatile or non-volatile) for storing data and programs. In some embodiments, the memory subsystem 604 may represent the entire virtual memory of the computer system 601, and may also include the virtual memory of other computer systems coupled to the computer system 601 or connected via a network. The memory subsystem 604 may be conceptually a single monolithic entity, but, in some embodiments, the memory subsystem 604 may be a more complex arrangement, such as a hierarchy of caches and other memory devices. For example, memory may exist in multiple levels of caches, and these caches may be further divided by function, so that one cache holds instructions while another holds non-instruction data, which is used by the processor or processors. Memory may be further distributed and associated with different CPUs or sets of CPUs, as is known in any of various so-called non-uniform memory access (NUMA) computer architectures. In some embodiments, the main memory or memory subsystem 604 may contain elements for control and flow of memory used by the CPU 602. This may include a memory controller 605.

Although the memory bus 603 is shown in FIG. 6 as a single bus structure providing a direct communication path among the CPUs 602, the memory subsystem 604, and the I/O bus interface 610, the memory bus 603 may, in some embodiments, comprise multiple different buses or communication paths, which may be arranged in any of various forms, such as point-to-point links in hierarchical, star or web configurations, multiple hierarchical buses, parallel and redundant paths, or any other appropriate type of configuration. Furthermore, while the I/O bus interface 610 and the I/O bus 608 are shown as single respective units, the computer system 601 may, in some embodiments, contain multiple I/O bus interface units 610, multiple I/O buses 608, or both. Further, while multiple I/O interface units are shown, which separate the I/O bus 608 from various communications paths running to the various I/O devices, in other embodiments some or all of the I/O devices may be connected directly to one or more system I/O buses.

In some embodiments, the computer system 601 may be a multi-user mainframe computer system, a single-user system, or a server computer or similar device that has little or no direct user interface, but receives requests from other computer systems (clients). Further, in some embodiments, the computer system 601 may be implemented as a desktop computer, portable computer, laptop or notebook computer, tablet computer, pocket computer, telephone, smart phone, mobile device, or any other appropriate type of electronic device.

It is noted that FIG. 6 is intended to depict the representative major components of an exemplary computer system 601. In some embodiments, however, individual components may have greater or lesser complexity than as represented in FIG. 6, components other than or in addition to those shown in FIG. 6 may be present, and the number, type, and configuration of such components may vary.

The programs described herein are identified based upon the application for which they are implemented in a specific embodiment of the disclosure. However, it should be appreciated that any particular program nomenclature herein is used merely for convenience, and thus the disclosure should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers, and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A computer-implemented method for matching clinical trial openings with candidates from a patient population, the method comprising: identifying a first clinical trial description;

generating annotations of the first clinical trial description, based on natural language processing techniques including Unstructured Information Management Architecture (UIMA), wherein the UIMA includes a language identification module using n-gram models for determining the language of the first clinical trial description; a linguistic analysis module for identifying parts of speech, syntactic position, and function; a dictionary module for defining terms and identifying synonyms; a named entity recognition module for identifying names, locations, and companies; a pattern recognition module for interpreting phrases and strings of numbers; a classification module for classifying the first clinical trial description according to content; and one or more custom annotators for identifying clinical features, disease states, diagnoses, one or more patient medications, one or more patient demographics, a patient-provider relationship, and a stage of disease progression; and wherein the annotations populate text indices, triple stores, and relational databases;

generating a first trial feature vector based on the annotations of the first clinical trial description, the first trial feature vector comprising a first array of values in a matrix, wherein the first array of values represents disease states, diagnoses, one or more patient medications, one or more patient demographics, a patient-provider relationship, and a stage of disease progression;

determining that a first value in the first array of values should be prioritized;

transforming the first value into a weighted vector value, wherein the weighted vector value is used to generate a second trial feature vector;

retrieving the first patient record and other patient records stored in a collection database, using a crawler, based on similarities between the annotations of the clinical trial description and contents of the patient records;

applying natural language processing techniques to the first patient record, the natural language processing techniques including Unstructured Information Management Architecture (UIMA), wherein the UIMA includes a language identification module using n-gram models for determining the language of the first patient record; a linguistic analysis module for identifying parts of speech, syntactic position and function; a dictionary module for defining terms and identifying synonyms; a named entity recognition module for identifying names, locations, and companies; a pattern recognition module for interpreting phrases and strings of numbers; a classification module for classifying the first patient record according to content; and one or more custom annotators for identifying clinical features, disease states, diagnoses, one or more patient medications, one or more patient demographics, a patient-provider relationship, and a stage of disease progression; wherein the UIMA generates annotations of the first patient record, the annotations populating one or more of text indices, triple stores, and relational databases;

generating a first patient feature vector based on the annotations of the first patient record, the first patient feature vector comprising the second array of values in a matrix, wherein the second array of values represents disease states, diagnoses, one or more patient medications, one or more patient demographics, a patient-provider relationship, and a stage of disease progression;

generating a comparison value based on the second trial feature vector and the first patient feature vector, wherein the comparison value represents a logical distance between the clinical trial feature vector and the patient feature vector;

displaying, via an interactive user interface, information about a patient associated with the patient record to a user based on the comparison value, wherein the information about the patient, including at least the comparison value, an identification of the patient, and a contact information for the patient, is displayed with information about other patients based on a plurality of comparison values generated from a plurality of patient records associated with the other patients, and wherein the interactive user interface allows the user to sort the information about the patient and the information about other patients based on sorting options comprising comparison values, patient name, and patient contact information;

receiving, through the interactive user interface, a threshold comparison value from the user; and displaying, via the interactive user interface, information about a set of patients, the set of patients associated with comparison values that meet the threshold comparison value, and wherein the set of patients is filtered and sorted based on patient name, contact information, geographic region, and disease type.

* * * * *